(12) United States Patent
Zambaux

(10) Patent No.: US 7,390,321 B2
(45) Date of Patent: Jun. 24, 2008

(54) CONNECTION HAVING LAMINAR FLOW FOR THE DELIVERY OF A SUBSTANCE

(75) Inventor: Jean-Pascal Zambaux, Riom (FR)

(73) Assignee: Advanced Technology Materials, Inc., Danbury, CT (US)

( * ) Notice: Subject to any disclaimer, the term of this patent is extended or adjusted under 35 U.S.C. 154(b) by 157 days.

(21) Appl. No.: 10/665,871

(22) Filed: Sep. 18, 2003

(65) Prior Publication Data

US 2005/0065495 A1 Mar. 24, 2005

(51) Int. Cl.
*A61B 19/00* (2006.01)
*A61M 39/04* (2006.01)
*B65D 37/00* (2006.01)

(52) U.S. Cl. .................. 604/408; 604/411; 604/414; 604/905; 604/244

(58) Field of Classification Search ......... 604/403–410, 604/6.15, 6.16, 903, 905, 246–249, 256, 604/264, 240–244, 533–539, 411–416, 262, 604/263, 222; 128/DIG. 24; 206/0.5, 0.6, 206/730, 745–6, 205, 207, 210, 213.1, 219, 206/222, 216, 223, 828, 543, 571–72, 363–366, 206/438; 220/200, 203.08, 500–502, 523–526, 220/202, 203.13, 203.19, 215, 229, 253, 220/255, 267, 62.11, 62.12, 694, 890; 222/541.1, 222/541.2, 544.4, 1, 5, 82, 541.4, 544–547, 222/522–525, 510, 630; 383/200, 202, 42–45, 383/47, 48, 51, 67, 78, 80, 100–103, 121, 383/127, 904, 906, DIG. 3

See application file for complete search history.

(56) References Cited

U.S. PATENT DOCUMENTS

| | | | | |
|---|---|---|---|---|
| RE25,129 | E | * | 2/1962 | Walter |
| 5,122,129 | A | * | 6/1992 | Olson et al. .................. 604/240 |
| 6,068,899 | A | * | 5/2000 | Osborn et al. .............. 428/35.2 |
| 6,391,014 | B1 | * | 5/2002 | Silverman ................... 604/415 |

* cited by examiner

*Primary Examiner*—Tatyana Zalukaeva
*Assistant Examiner*—Leslie Deak
(74) *Attorney, Agent, or Firm*—Vincent K. Gustafson; Intellectual Property Technology Law; David M. Shofi

(57) ABSTRACT

In one embodiment, a method includes puncturing, with a piercing element of a hollow connector, an opening of a membrane that encloses the hollow connector in a gas that is essentially sterile. The puncturing of the opening of the membrane generates a laminar flow of the gas along sides of the opening. The method also includes transferring the fluids, through the opening with the piercing element of the hollow connector.

54 Claims, 5 Drawing Sheets

CONNECTION HAVING LAMINAR FLOW FOR THE DELIVERY OF A SUBSTANCE

TECHNICAL FIELD

This invention generally relates delivery of substances. More particular, the invention relates to a connection having a laminar flow for the delivery of a substance.

BACKGROUND

The sterile transfer of various substances is important across a number of different industries in order to provide freedom from contaminants in the ambient environment. A number of different techniques have been developed to keep the transferring fluid free of such contaminants. A typical approach is to transfer fluid through male and female connectors. Such connectors include exposed surfaces that are wiped with an antiseptic prior to the connection and transfer of fluid from the male connector to the female connector. Another approach is to include covers on the connectors that are removed prior to the connection and transfer of fluid.

However, these conventional approaches may not preclude the introduction of contaminants into the fluid. In particular, an individual is involved in the cleaning or removal of the protective covers. Even using protective surgical gloves, the individual may make incidental contact with the exposed connectors during the cleaning of the surfaces or removal of the protective covers on such surfaces, thereby transferring contaminants on the surgical gloves onto the surfaces.

Moreover, once the surfaces are cleaned or the protective covers are removed, such surfaces are exposed to the ambient environment. In particular, despite a quick coupling of the two different connectors subsequent to the cleaning/removal, a number of different contaminants may come into contact with the surface. Accordingly, such contaminants may infiltrate the fluids during the transfer between the connectors.

SUMMARY

Systems, apparatuses and methods for a connection having a laminar flow for the delivery of a substance are now described. As further described below, embodiments of the invention allow for an approximately sterile transfer of a substance from a first container to a second container. Embodiments of the invention provide for a laminar flow of a gas during a connection between the first container and the second container to preclude the infiltration of contaminants from the ambient environment. As further described below, a gas is housed at a pressure in a membrane surrounding a connector of the first container. Such pressure allows for a laminar flow of the gas along the sides of an opening created by the connector during the transfer of the substance from the first container to the second container.

In one embodiment, a method includes puncturing, with a piercing element of a hollow connector, an opening of a membrane that encloses the hollow connector in a gas that is essentially sterile. The puncturing of the opening of the membrane generates a laminar flow of the gas along sides of the opening. The method also includes transferring the fluids, through the opening with the piercing element of the hollow connector.

In an embodiment, a method includes enclosing a connector within a membrane housing. The method also includes inserting a gas that is essentially sterile into the membrane housing at a gas pressure such that after a piercing element of the connector pierces an opening in the membrane housing. A laminar flow of the gas is generated along sides of the opening. The method includes sealing the membrane housing from an environment external to the membrane housing.

In an embodiment, an apparatus includes a hollow connector having an interior wall defining a chamber for the passageway of fluids. The hollow connector comprises a distal end and a proximal end. The distal end is configured to engage a container and the proximal end has an aperture there through for the egress of the fluids from the container. The apparatus also includes a membrane having an interior surface defining a chamber for housing the hollow connector with a gas that is essentially sterile, wherein the gas has a pressure of greater than about 1 atm inside the membrane.

In one embodiment, a system includes a first delivery assembly comprising a first container having an opening. The first container is to hold a liquid. The first delivery assembly includes a hollow connector having an interior wall defining a chamber for a passageway for the liquid. The hollow connector comprises a distal end and a proximal end. The distal end is configured to engage the first container and the proximal end has an aperture there through for the egress of the liquid from the container. The first delivery assembly includes a membrane having an interior surface defining a chamber for housing the hollow connector with a gas that is essentially sterile, wherein the gas has a pressure of greater than about 1 atm inside the membrane.

In an embodiment, a kit includes a delivery assembly comprising a hollow connector having an interior wall defining a chamber for the passageway of fluids. The hollow connector comprises a distal end and a proximal end. The distal end is configured to engage a container and the proximal end has an aperture there through for the egress of the fluids from the container. The delivery assembly comprises a membrane having an interior surface defining a chamber for housing the hollow connector with a gas that is essentially sterile, wherein the gas has a pressure of greater than about 1 atm inside the membrane. The kit also includes packaging material and instructions or indicia located on the packaging material or inside the packaging material.

BRIEF DESCRIPTION OF THE DRAWINGS

Embodiments of the invention may be best understood by referring to the following description and accompanying drawings which illustrate such embodiments. The numbering scheme for the Figures included herein are such that the leading number for a given reference number in a Figure is associated with the number of the Figure. For example, a system 100 can be located in FIG. 1. However, reference numbers are the same for those elements that are the same across different Figures. In the drawings.

DETAILED DESCRIPTION

Methods, apparatuses and systems for different embodiments for a connection having a laminar flow for the delivery of a substance are described. References in the specification to "one embodiment", "an embodiment", "an example embodiment", etc., indicate that the embodiment described may includes a particular feature, structure, or characteristic, but every embodiment may not necessarily include the particular feature, structure, or characteristic. Moreover, such phrases are not necessarily referring to the dame embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

A number of figures show block diagrams of systems and apparatus for a connection having a laminar flow for the delivery of a substance, in accordance with embodiments of the invention. A number of figures show flow diagrams illustrating operations for a connection having a laminar flow for the delivery of a substance. The operations of the flow diagrams will be described with references to the systems/apparatus shown in the block diagrams. However, it should be understood that the operations of the flow diagrams could be performed by embodiments of systems and apparatus other than those discussed with reference to the block diagrams, and embodiments discussed with reference to the systems/apparatus could perform operations different than those discussed with reference to the flow diagrams.

Figure 1:
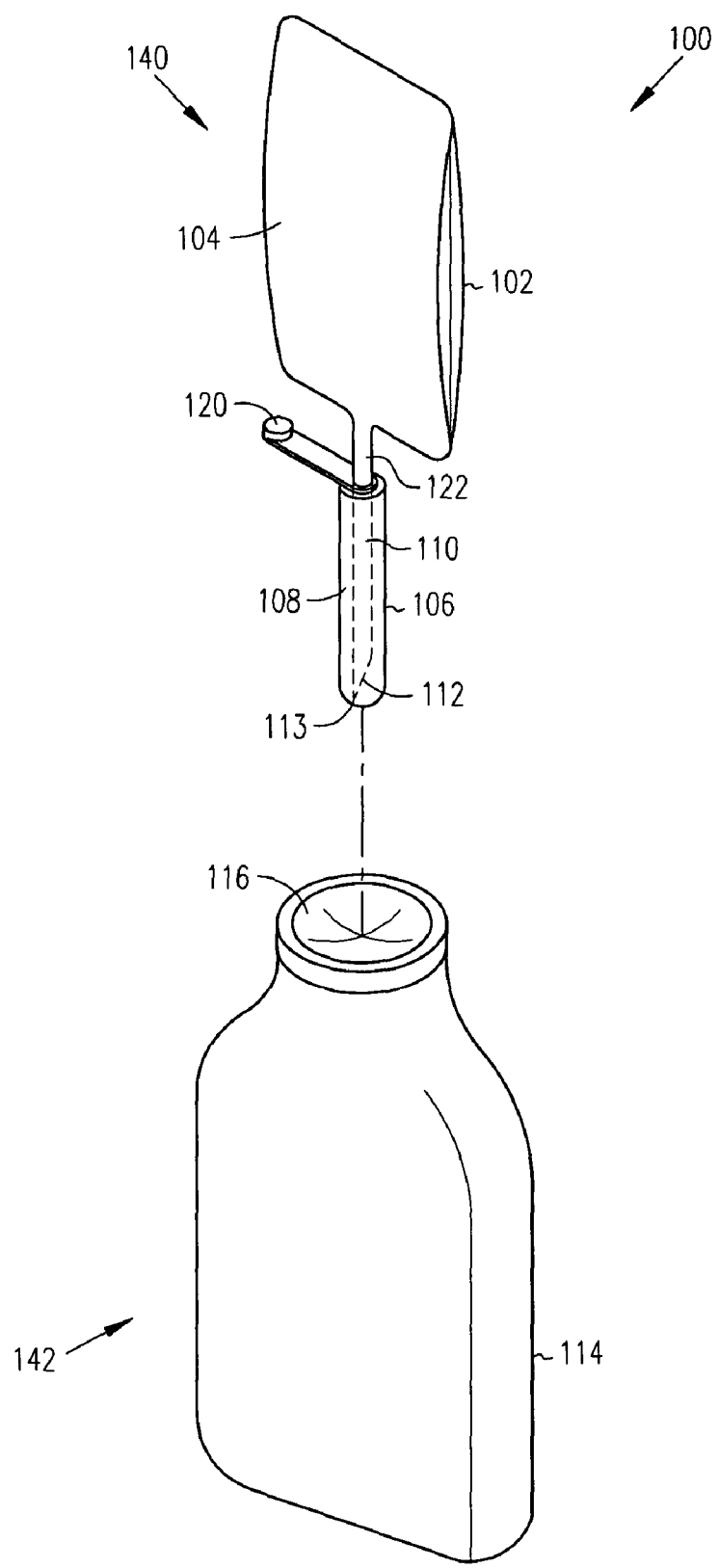
FIG. 1 illustrates a system for a connection having a laminar flow for the delivery of a substance, according to one embodiment of the invention.

FIG. 1 illustrates a system for a connection having a laminar flow for the delivery of a substance, according to one embodiment of the invention. In particular, FIG. 1 illustrates a system 100 that includes a first delivery assembly 140 that transfers a substance 104 (e.g., a fluid or a liquid) to a second delivery assembly 142. The first delivery assembly 140 includes a first container 102, a first connector 110, a coupling 122, a membrane 106 and a latch 120. The second delivery assembly 142 includes a second container 114 and a second connector 116. While the system 100 may have a number of different applications, in one embodiment, the system 100 is for the transfer of bodily fluids. For example, the substance 104 may be blood. Accordingly, the substance 104 may be blood, wherein the first container 102 and the second container 114 are blood bags. In one embodiment, the substance 104 may be bodily fluids that includes at least one of macrophages, B lymphocytes, cytotoxic T lymphocytes, plasma cells, helper cells, B lymphocytes, antibodies, erythrocytes, leukocytes, red blood cells, white blood cells, and platelets. In one embodiment, the substance 104 may be bodily fluids that includes arterial blood, banked blood, cord blood, defibrinated blood, laky blood, oxalated blood, or whole blood.

The first container 102 and the second container 114 may be made from any suitable material. In an embodiment, the second connector 116 is a cap that may be made of a number of different types of material. For example, the second connector 116 may be different types of silicon.

With regard to the membrane 106, such membrane may be made from any suitable material. In one embodiment, the membrane 106 is flexible. In an embodiment, the membrane 106 is made of any suitable material having a property where upon removal of an extending force, it is capable of substantially recovering its original size and shape and/or exhibits a significant retractive force. As such, the membrane 106 may be made of any suitable type of stretchable, collapsible and/or elastic material. As used herein, the term "collapsible" refers to a material that may fold down into a more compact shape.

The membrane 106 may be manufactured from any suitable material. Suitable materials include, e.g., films, polymers, thermoplastic polymers, homopolymers, copolymers, block copolymers, graft copolymers, random copolymers, alternating copolymers, terpolymers, metallocene polymers, nonwoven fabric, spunbonded fibers, meltblown fibers, polycellulose fibers, polyester fibers, polyurethane fibers, polyolefin fibers, polyamide fibers, cotton fibers, copolyester fibers, open cell foam, polyurethane, polyvinyl chloride, polyethylene, metals, alloys, fiberglass, glass, plastic (e.g., polyethylene (PE), polypropylene (PP), polyvinyl chloride (PVC), polyethylene terephtalate (PET) and Teflon), rubber, and combinations or mixtures thereof.

In an embodiment, the first connector 110 is a hollow connector that has an interior wall defining a chamber for the passageway of the substance 104 from the first container 102. The first container 102 is coupled to a distal end of the first connector 110 through the coupling 122. While the first container 102 may be coupled to the first connector 110 a number of approaches, in one embodiment, the first container 102 may be coupled to the first connector 110 via a threaded connector. In an embodiment, the first container 102 may be coupled to the first connector 110 by a welding process.

The latch 120 is between the coupling 122 and the first connector 110. The latch 120 may be a clamp or break valve. For example, the coupling 122 may include a cover that is broken by a break valve when the break valve is rotated. Therefore, the substance 104 does not dispense into the first connector 110 until the latch 120 is rotated to allow for such dispensing. In an embodiment, the first container 102, the coupling 122 and the latch 120 may be detached from the first connector 110 and the membrane 106 until the operation of the system 100. The first connector 110 includes a piercing element 112 opposite the part that is coupled to the passageway 122 through the clamp 120. The piercing element 112 includes an aperture for the delivery of the substance 104 out from the first delivery assembly 140.

As shown, the membrane 106 protects the first connector 110 from the ambient environment by forming a membrane housing that surrounds the first connector 110. The membrane 106 has an interior surface that defines a chamber for housing the connector 110. In particular, the membrane 106 houses or encloses the first connector 110 within a gas 108, thereby isolating the first connector 110 from contaminants in the ambient environment that is external to the membrane 106. In one embodiment, the gas 108 is essentially sterile. In an embodiment, the gas 108 is more than about 95% sterile. In one embodiment, the gas 108 may be oxygen, nitrogen, argon, etc. In an embodiment, the gas 108 may be a combination of such gases. A location 113 of the membrane 106 is adjacent to the piercing element 112. In one embodiment, the piercing element 112 is hollow and includes an opening or aperture at the point that is adjacent to the location 113 of the membrane 106. Accordingly, the piercing element 112 may delivery the substance 104 in the first container 102 to the container 114 through the connector 116. For example, the piercing element 112 may be a needle or a cannula to deliver a fluid (e.g., blood) into the container 114.

As further described in more detail below in conjunction with the description of FIG. 3, in one embodiment, the location 113 of the membrane 106 includes a cut within an inner lining of the membrane 106. Such a cut assists in the puncture or piercing of the membrane 106 at the location 113 and precludes the puncture or tearing of the membrane 106 in other locations.

Figure 6:
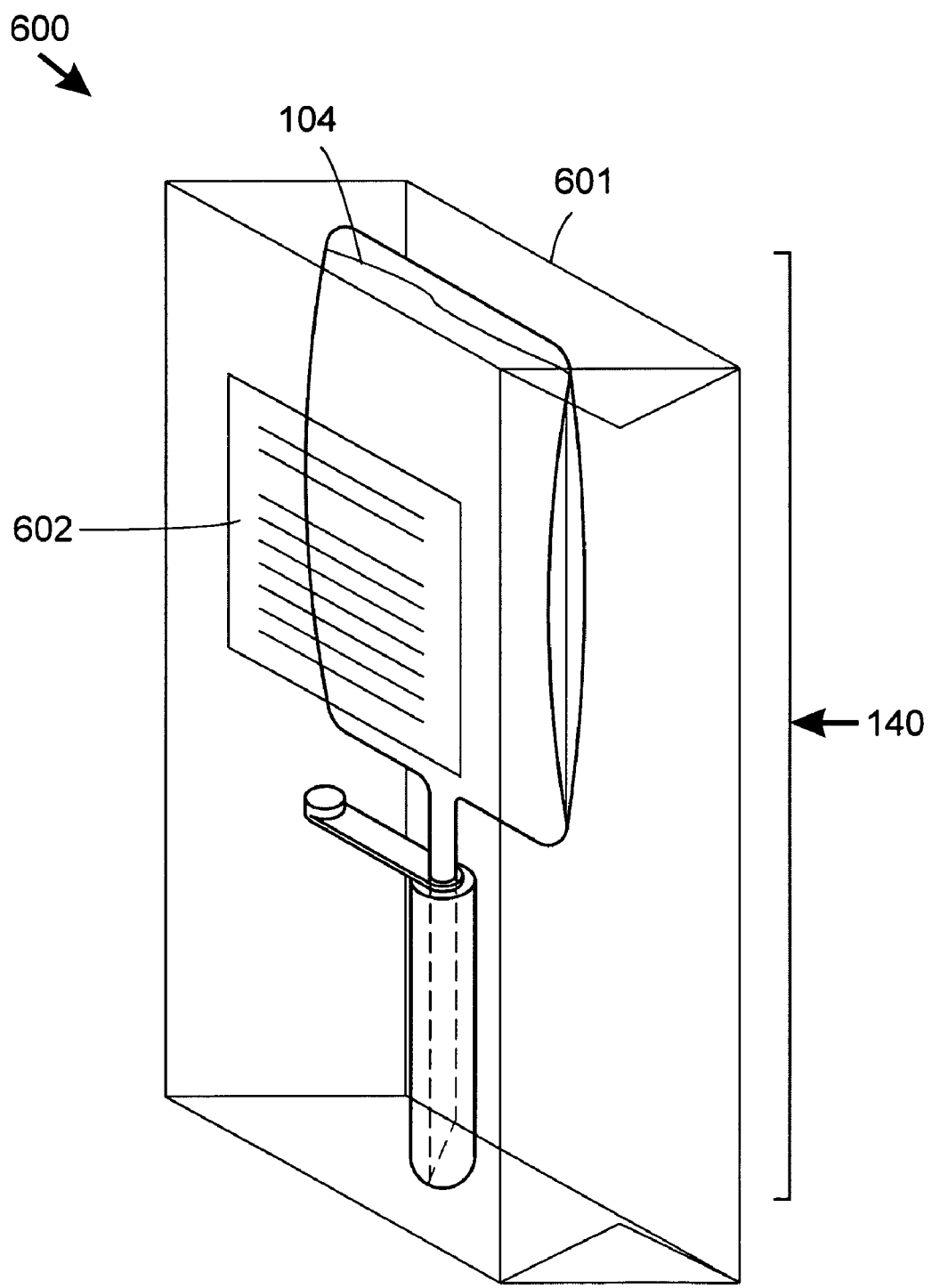
FIG. 6 illustrates a perspective view of a kit comprising a delivery assembly according to the present invention disposed within a package having instructions or indicia disposed on the packaging material.

In an embodiment, at least part of the system 100 may be incorporated as a kit 600 such as illustrated in FIG. 6. For example, the kit 600 may include the first delivery assembly 140 along with packaging material 601 and instructions or indicia 602 located on the packaging material 601 or inside the packaging material 601. In one such embodiment, the substance 104 is included in such a kit 600.

Figure 2A:
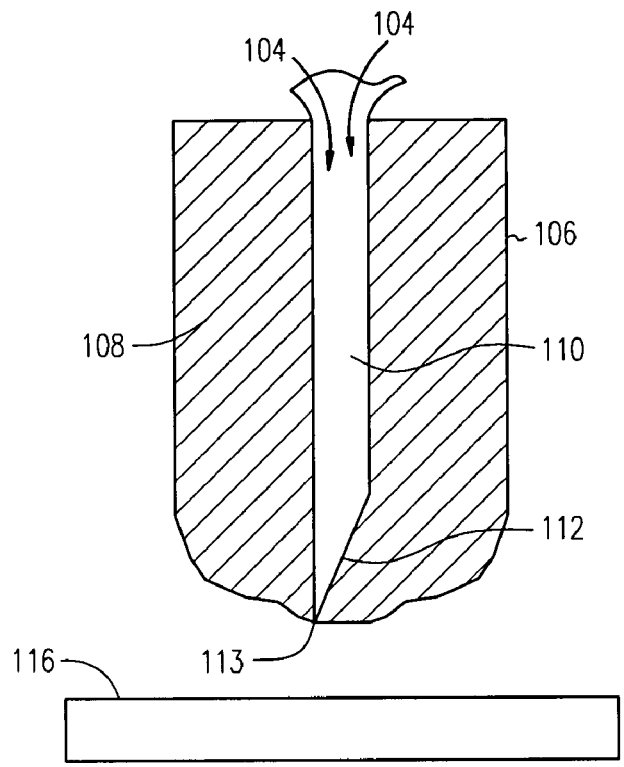
FIGS. 2A-2B illustrate a connector housed in a membrane to provide a connection having a laminar flow for the delivery of a substance, according to one embodiment of the invention.
Figure 2B:
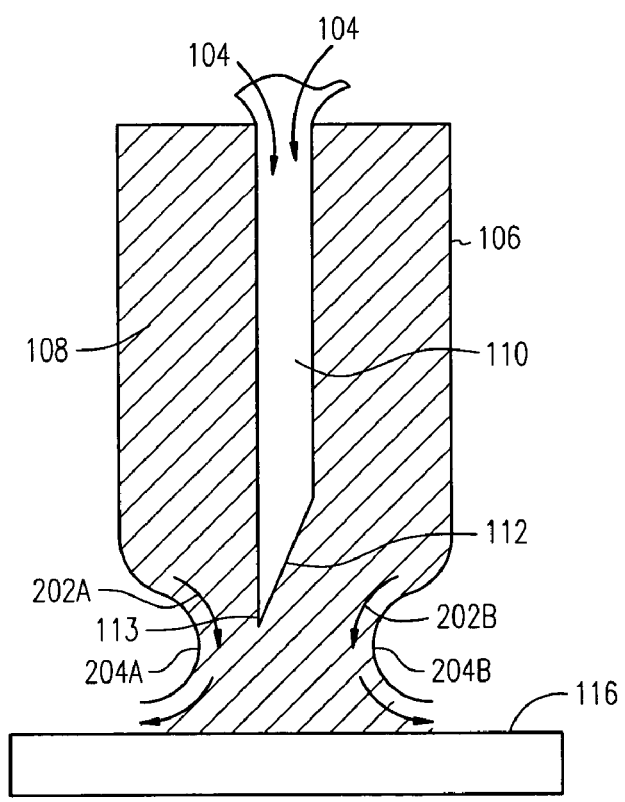

Moreover as is now described conjunction with the description of FIGS. 2A-2B, the gas 108 is set at a pressure such that after the piercing element 112 punctures the membrane 106 at the location 113, a laminar flow of the gas 108 insulates or buffers the piercing element 112 and the substance 104 (being dispensed through piercing element 112) from contaminants in the ambient environment that is external to the membrane 106. In particular, FIGS. 2A-2B illustrate a connector housed in a membrane to provide a connection having a laminar flow for the delivery of a substance, according to one embodiment of the invention.

FIG. 2A illustrates a part of the first delivery assembly 140 and a part of the second delivery assembly 142 prior to the piercing element 112 piercing the membrane 106 at the location 113. FIG. 2B illustrates those parts of the first delivery assembly 140 and the second delivery assembly 142 subsequent to the piercing element 112 piercing the membrane 106 at the location 113. In particular, FIG. 2B illustrates the laminar flow of the gas 108 after the piercing element 112 has pierced the membrane 106 at the location 113.

As shown, FIG. 2A illustrates the membrane 106 housing the first connector 110 in the gas 108 at a gas pressure. The first connector 110 is to deliver the substance 104 through the second connector 116. In particular, the first connector 110 is to deliver the substance 104 through the piercing element 112 through an opening in the membrane 106 at the location 113.

FIG. 2B illustrates the opening in the membrane 106 at the location 113. The pressure of the gas 108 is such that a first laminar flow 202A and a second laminar flow 202B are created along a first side 204A and a second side 204B, respectively, of an opening in the membrane 106 at the location 113. In particular, such an opening was created by the piercing element 112 piercing the membrane 106 at the location 113. As shown, the first laminar flow 202A and the second laminar flow 202B preclude contaminants in the ambient environment from coming into contact with the transfer of the substance 104 from the first connector 110.

The pressure of the gas 108 may be at any level that allows for the laminar flow of the gas 108 along the sides of the opening created by the piercing element 112. In one embodiment, the pressure of the gas 108 is in a range of approximately five to 30 millibars. In an embodiment, the gas 108 in the membrane housing has a pressure greater than about 1.05 atm. In an embodiment, the gas 108 in the membrane housing has a pressure of greater than about 1.1 atm.

Figure 3:
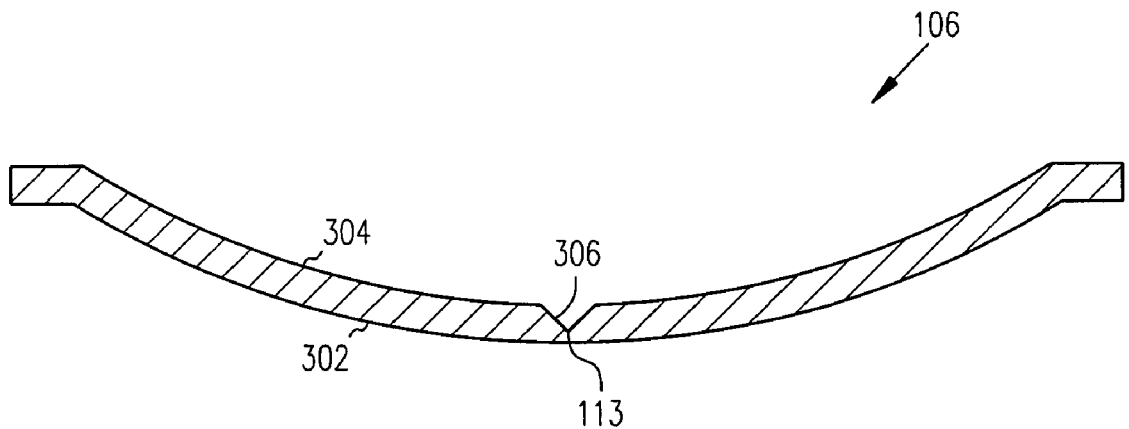
FIG. 3 illustrates a membrane that houses a connector to provide a connection having a laminar flow for the delivery of a substance, according to one embodiment of the invention.

FIG. 3 illustrates a membrane that houses a connector to provide a connection having a laminar flow for the delivery of a substance, according to one embodiment of the invention. In particular, FIG. 3 illustrates one embodiment of the membrane 106. The membrane 106 includes an exterior surface 302 and an interior surface (inner lining) 304. Additionally, the membrane 106 includes a cut 306 in the interior surface 304 at the location 113 of the membrane 106. The cut 306 is a partial slit or cut in the interior surface 306 that assists in the piercing of the membrane 106 by the piercing element 112. Moreover, the cut 306 allows the piercing of the membrane 106 at the location 113 and to preclude the tearing or opening of the membrane 106 at other locations of the membrane 106. Accordingly, having only one opening (at the location 113) in the membrane 106 allows for the laminar flow of the gas 108 based on the pressure of such gas. In one embodiment, the thickness of the membrane 106 is in a range of approximately 15 to 200 microns.

Figure 4:
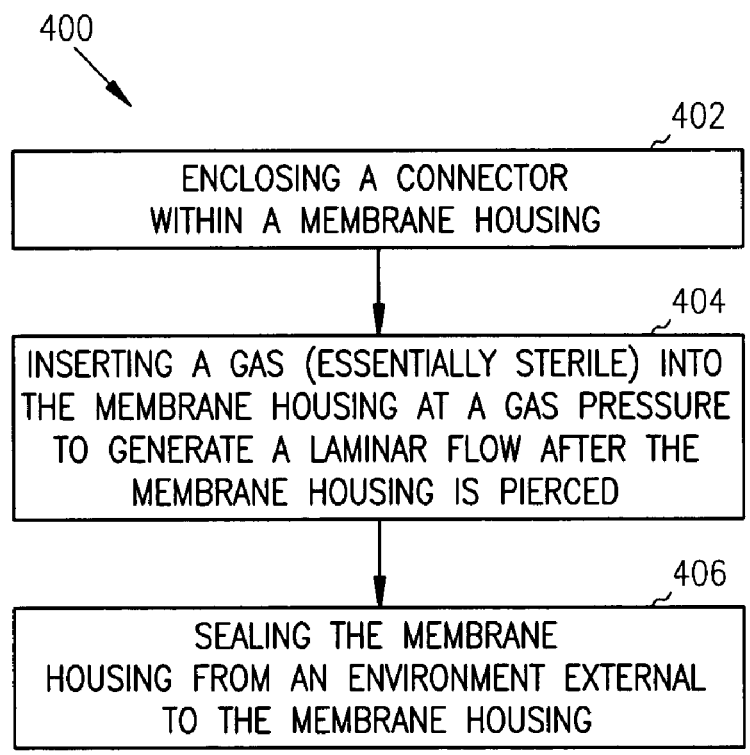
FIG. 4 illustrates a flow diagram for generating a connector enclosed in a membrane to provide a connection having a laminar flow for the delivery of a substance, according to one embodiment of the invention.

One embodiment for generating the first connector 110 housed in a membrane 106 is now described. In particular, FIG. 4 illustrates a flow diagram for generating a connector enclosed in a membrane to provide a connection having a laminar flow for the delivery of a substance, according to one embodiment of the invention.

In block 402 of the flow diagram 400, a connector is enclosed/housed within a membrane housing. With reference to the embodiment of FIG. 1, the membrane 106 encloses or houses the connector 106. In an embodiment, the membrane 106 encloses the first connector 110 using a heating element to weld the membrane 106 to the connector 110 at the end that is opposite the end adjacent to the piercing element 112. The membrane 106 encloses the first connector 110 such that connector is isolated from the ambient environment (including contaminants therein). Control continues at block 404.

In block 404, a gas is inserted into the membrane housing (formed by the membrane around the connector) at a gas pressure to generate a laminar flow after the membrane housing is pierced. With reference to the embodiment of FIG. 1, the gas 108 is inserted into the membrane housing (formed by the membrane 106 around the first connector 110) at a gas pressure to generate a laminar flow after the membrane housing is pierced. In one embodiment, the gas 108 is inserted into the membrane housing through an approximately sterile needle that delivers the gas 108 by piercing the membrane 106.

As described above, the pressure of the gas 108 may be at any level that allows for the laminar flow of the gas 108 along the sides of the opening created by the piercing element 112. In one embodiment, the pressure of the gas 108 is in a range of approximately five to 30 millibars. Control continues at block 406.

In block 406, the membrane housing is sealed from an environment external to the membrane housing. With reference to the embodiment of FIG. 1, the membrane 106 that is housing the connector 110 is sealed from the environment external to the membrane 106. In one embodiment, the composition of the membrane 106 is such that the opening created by the needle to deliver the gas 108 is sealed off after the needle is removed from the opening in the membrane 106. The operations of the flow diagram 400 are complete.

The generation of the connector enclosed in a membrane to provide a connection having a laminar flow for the delivery of a substance is not limited to the operations and/or the order of such operations illustrated in the flow diagram 400. For example, in another embodiment, the connector 110 is placed in an environment of the gas at the given gas pressure. In this environment, the connector 110 is then enclosed within a membrane housing.

Figure 5:
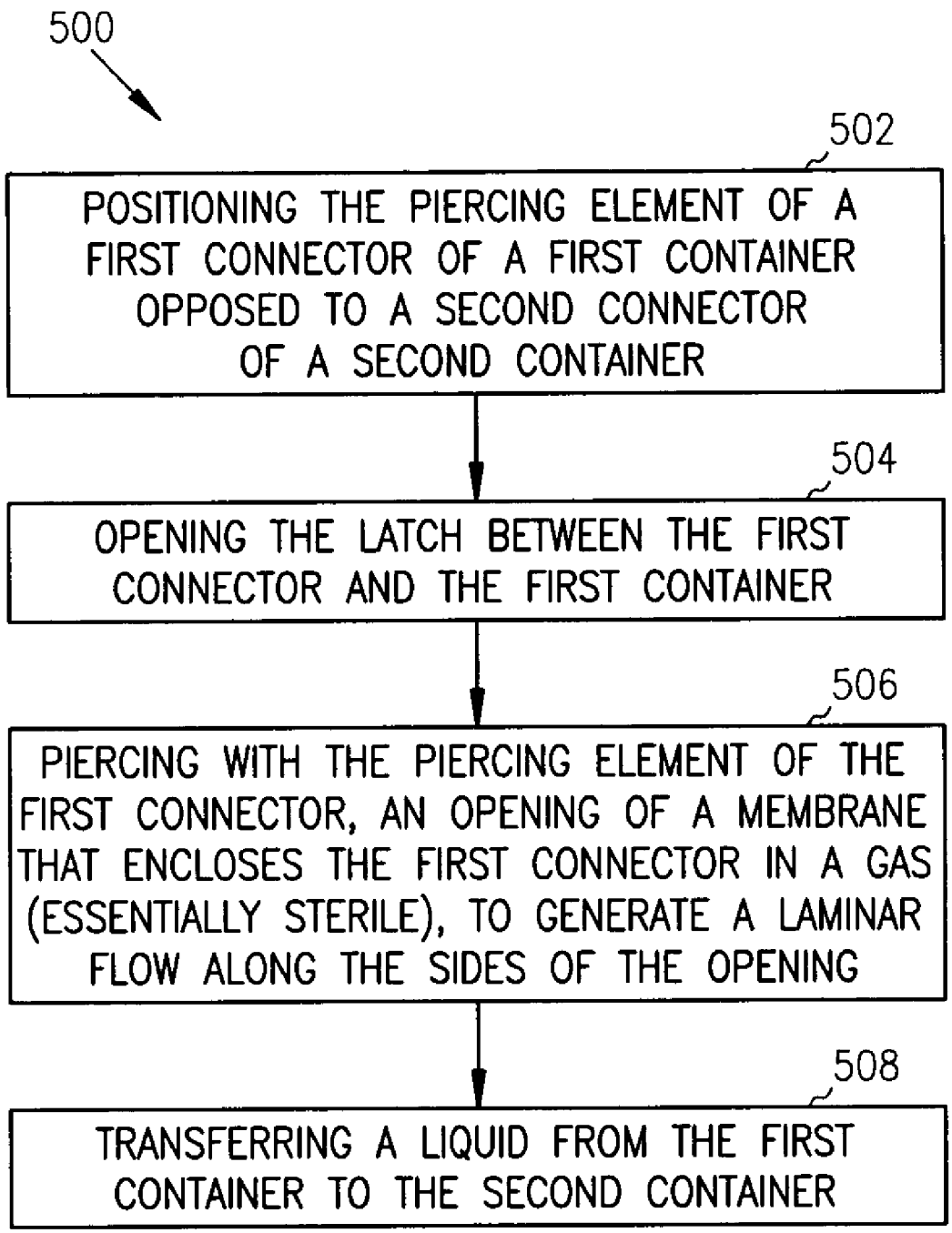
FIG. 5 illustrates a flow diagram for delivery of a substance through a connection having a laminar flow, according to one embodiment of the invention.

One embodiment for delivery of the substance 104 through a connection having a laminar flow in the system 100 is now described. In particular, FIG. 5 illustrates a flow diagram for delivery of a substance through a connection having a laminar flow, according to one embodiment of the invention.

In block 502 of the flow diagram 500, the piercing element of the first connector of the first container is positioned opposed to a second connector of a second container. With reference to the embodiment of FIGS. 2A-2B, the piercing element 112 of the first connector 110 is positioned opposed to the second connector 116. Control continues at block 504.

In block 504, a latch between the first connector and the first container is opened. With reference to the embodiment of FIG. 1, the latch 120 between the first connector 110 and the first container 102 is opened. Accordingly, the substance 104 in the first container 102 is allowed to flow into the first connector 110. As described above, the latch 120 may be a clamp or break valve. Control continues at block 506.

In block 506, an opening is pierced, with the piercing element of the first connector, in a membrane that encloses the first connector in a gas to generate a laminar flow along the sides of the opening. With reference to the embodiment of FIG. 2B, the piercing element 112 pierces the opening in the membrane 106, thereby generating a first laminar flow 202A and a second laminar flow 202B along the first side 204A and the second side 204B, respectively, of the opening in the membrane 106. Control continues at block 508.

In block 508, a substance is transferred from the first container to the second container. With reference to the embodiment of FIG. 1, the substance 104 is transferred from the first container 102 to the second container 114 through the first connector 110 and through the second connector 116. As shown in FIG. 2B, the creation of the first laminar flow 202A and the second laminar flow 202B of the gas 108 precludes contaminants in the ambient environment from coming into contact with the transfer of the substance 104 from the first connector 110 through the second connector 116 into the second container 114. The operations of the flow diagram 500 are complete.

As used herein, the term "elastic," or "elastomeric" refers to that property of a material where upon removal of an extending force, it is capable of substantially recovering its original size and shape and/or exhibits a significant retractive force.

As used herein, the term "stretch," or "stretchable" refers to a material that is either elastic or extensible. That is, the material is capable of being extended, deformed, or the like, without breaking, and may or may not significantly retract after removal of an extending force. In an embodiment, the stretchable material can optionally be biaxial stretchable.

As used herein, the term "biaxial stretch" or "biaxial stretchable" refers to a material having stretchability in two directions perpendicular to one another, e.g. stretchability in a machine direction and in a cross machine direction, or in a longitudinal direction (front to back) and a lateral direction (side to side).

As used herein, the term "film" refers to a thermoplastic film made using a film extrusion and/or foaming process, such as a cast film or blown film extrusion process. For the purposes of the present invention, the term includes nonporous films as well as microporous films. Films may be vapor permeable or vapor impermeable, and function as liquid barriers under normal use conditions.

As used herein, the term "thermoplastic" refers to uncrosslinked polymers of a thermally sensitive material which flows under the application of heat or pressure.

As used herein, the term "polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

As used herein, the term "metallocene polymers" refers to those polymer materials that are produced by the polymerization of at least ethylene using metallocenes or constrained geometry catalysts, a class of organometallic complexes, as catalysts.

As used herein, the term "nonwoven" and "nonwoven web" refer to fibrous materials and webs of fibrous material which are formed without the aid of a textile weaving or knitting process.

As used herein, "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced.

As used herein, "meltblown fiber" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter (the average microfiber diameter is not greater than about 100 microns, for example, having an average diameter of from about 0.5 microns to about 50 microns, more particularly, microfibers may have an average diameter of from about 4 microns to about 40 microns).

Thus, methods, apparatuses and systems for a connection having a laminar flow for the delivery of a substance have been described. Although the present invention has been described with reference to specific exemplary embodiments, it will be evident that various modifications and changes may be made to these embodiments without departing from the broader spirit and scope of the invention. Therefore, the specification and drawings are to be regarded in an illustrative rather than a restrictive sense.

What is claimed is:

1. An apparatus comprising:
    a hollow connector having an interior wall defining a fluid chamber for the passage of fluids, wherein the hollow connector comprises an inlet end and an outlet end, wherein the inlet end is configured to engage a container and the outlet end has an aperture therethrough for the egress of the fluids from the container; and
    a membrane having an interior surface defining a housing chamber housing the hollow connector and a gas that is essentially sterile,
    wherein the gas inside the housing chamber has a pressure sufficient to generate a laminar flow outward from an opening defined in the membrane upon piercing of the membrane by the connector.

2. The apparatus of claim 1, wherein the gas comprises oxygen, nitrogen, argon, or a combination thereof.

3. The apparatus of claim 1, wherein the gas is more than about 95% sterile.

4. The apparatus of claim 1, wherein the gas has a pressure of greater than 1.05 atm when inside the housing chamber.

5. The apparatus of claim 1, wherein the gas has a pressure of greater than 1.1 atm when inside the housing chamber.

6. The apparatus of claim 1, wherein the membrane has a thickness of less than about 200 microns.

7. The apparatus of claim 1, wherein the membrane has a thickness of between about 15 microns to about 200 microns.

8. The apparatus of claim 1, wherein the interior surface of the membrane has a partial slit or cut that does not penetrate completely through the membrane.

9. The apparatus of claim 1, further comprising a container that is connected to the inlet end of the hollow connector.

10. The apparatus of claim 9, further comprising a latch coupled between the container and the hollow connector.

11. The apparatus of claim 1, wherein the hollow connector comprises a piercing element.

12. The apparatus of claim 1, wherein the container comprises a flexible bag.

13. The apparatus of claim 1, wherein the hollow connector is configured to engage the container via a threaded connection.

14. The apparatus of claim 1, wherein the outlet end of the hollow connector is further configured to engage a second container, wherein the second container is to receive, through the connector, the fluids from the container.

15. The apparatus of claim 1, wherein the fluids comprise bodily fluids.

16. The apparatus of claim 15, wherein the bodily fluids comprise blood.

17. The apparatus of claim 15, wherein the bodily fluids comprise at least one of macrophages, B lymphocytes, cytotoxic T lymphocytes, plasma cells, helper cells, B lymphocytes, antibodies, erythrocytes, leukocytes, red blood cells, white blood cells, and platelets.

18. The apparatus of claim 15, wherein the bodily fluids comprise arterial blood, banked blood, cord blood, defibrinated blood, laky blood, oxalated blood, or whole blood.

19. The apparatus of claim 1, wherein the hollow connector comprises a piercing element disposed within the housing chamber along the outlet end.

20. The apparatus of claim 1, wherein the gas has a pressure of greater than 1 atm when inside the housing chamber.

21. A system comprising:
   a first delivery assembly comprising:
      a first container having an opening, the first container to hold a liquid;
      a hollow connector having an interior wall defining a fluid chamber for the passage of the liquid, wherein the hollow connector comprises an inlet end and an outlet end, wherein the inlet end is configured to engage the first container and the outlet end has an aperture therethrough for the egress of the liquid from the container; and
      a membrane having an interior surface defining a housing chamber housing the hollow connector and a gas that is essentially sterile, wherein the gas inside the housing chamber has a pressure sufficient to generate a laminar flow outward from an opening defined in the membrane upon piercing of the membrane by the connector.

22. The system of claim 21 further comprising a second delivery assembly, wherein the second delivery assembly comprises:
   a different connector configured to engage the hollow connector; and
   a second container to receive, through the second connector, the liquid from the first container through the aperture.

23. The system of claim 21, wherein the gas comprises oxygen, nitrogen, argon, or a combination thereof.

24. The system of claim 21, wherein the gas is more than about 95% sterile.

25. The system of claim 21, wherein the gas has a pressure of greater than 1.05 atm when inside the housing chamber.

26. The system of claim 21, wherein the gas has a pressure of greater than 1.1 atm when inside the housing chamber.

27. The system of claim 21, wherein the membrane has a thickness of less than about 200 microns.

28. The system of claim 21, wherein the membrane has a thickness of between about 15 microns to about 200 microns.

29. The system of claim 21, wherein the interior surface of the membrane has a partial slit or cut that does not penetrate completely through the membrane.

30. The system of claim 21, wherein the first delivery assembly comprises a latch coupled between the first container and the hollow connector.

31. The system of claim 21, wherein the hollow connector comprises a piercing element.

32. The system of claim 21, wherein the first container comprises a flexible bag.

33. The system of claim 21, wherein the hollow connector is configured to engage the first container via a threaded connection.

34. The system of claim 21, wherein the liquid comprise bodily fluids.

35. The system of claim 34, wherein the bodily fluids comprise blood.

36. The system of claim 34, wherein the bodily fluids comprise at least one of macrophages, B lymphocytes, cytotoxic T lymphocytes, plasma cells, helper cells, B lymphocytes, antibodies, erythrocytes, leukocytes, red blood cells, white blood cells, and platelets.

37. The system of claim 34, wherein the bodily fluids comprise arterial blood, banked blood, cord blood, defibrinated blood, laky blood, oxalated blood, or whole blood.

38. The system of claim 21, wherein the hollow connector comprises a piercing element disposed within the housing chamber along the outlet end.

39. The system of claim 21, wherein the gas has a pressure of greater than 1 atm when inside the housing chamber.

40. A kit comprising:
   a delivery assembly comprising a hollow connector having an interior wall defining a fluid chamber for the passage of fluids, wherein the hollow connector comprises an inlet end and an outlet end, wherein the inlet end is configured to engage a container and the outlet end has an aperture therethrough for the egress of the fluids from the container, the delivery assembly comprising a membrane having an interior surface defining a housing chamber housing the hollow connector and a gas that is essentially sterile, wherein the gas inside the housing chamber has a pressure sufficient to generate a laminar flow outward from an opening defined in the membrane upon piercing of the membrane by the connector;
   packaging material; and
   instructions or indicia located on the packaging material or inside the packaging material.

41. The kit of claim 40, further comprising a fluid located in the container.

42. The kit of claim 40, wherein the interior surface of the membrane has a partial slit or cut that does not penetrate completely through the membrane.

43. The kit of claim 40, wherein the delivery assembly comprises a latch coupled between the container and the hollow connector.

44. The kit of claim 40, wherein the hollow connector comprises a piercing element disposed within the housing chamber along the outlet end.

45. The kit of claim 40, wherein the gas has a pressure of greater than 1 atm when inside the housing chamber.

46. The kit of claim 40, wherein the hollow connector is configured to engage the container via a threaded connection.

47. A method comprising the steps of:
   connecting a source container adapted to hold a fluid to an inlet end of a hollow connector comprising a piercing element adjacent to an outlet end of the hollow connector, with the piercing element disposed in an essentially sterile gas at a pressure greater than about 1 atm, the gas being contained by a membrane;

positioning the outlet end of the hollow connector adjacent to a target container;

puncturing an opening in the membrane with the piercing element, wherein puncturing the opening generates a laminar flow of the gas along the sides of the opening; and extending at least a portion of the hollow connector into the target container.

48. The method of claim 47, wherein the source fluid contains a fluid, and the method further comprising the step of transferring at least a portion of the fluid from the source container through the hollow connector into the target container.

49. The method of claim 47, further comprising the step of opening a latch between the hollow connector and the source container.

50. The method of claim 47, wherein the membrane initially comprises a partial slit or cut that does not penetrate completely through the membrane, and wherein the step of puncturing an opening in the membrane comprises puncturing the opening along the partial slit or cut.

51. A method comprising the steps of:

enclosing a piercing element of a hollow connector within a membrane housing sealed from an external environment, the piercing element being adapted to puncture the membrane housing; and inserting a gas that is essentially sterile into the membrane housing at a gas pressure of greater than about 1 atm to generate, when the piercing element punctures an opening in the membrane housing, a laminar flow of gas out of the membrane housing along sides of the opening.

52. The method of claim 51, the gas pressure comprises a gage pressure of greater than about 5 millibars.

53. The method of claim 51, further comprising creating a partial slit or cut in an inner lining of the membrane housing, with the partial slit or cut not penetrating an outer lining of the membrane housing.

54. The method of claim 53, wherein creating the partial slit or cut in the inner lining of the membrane housing comprises creating the partial slit or cut at a location in the inner lining aligned with the piercing element to facilitate puncture by the piercing element of the membrane housing along the partial slit or cut.

* * * * *